United States Patent [19]

Dai et al.

[11] 4,282,383

[45] Aug. 4, 1981

[54] PROCESS FOR THE AUTOXIDATION OF CYCLOHEXYLBENZENE TO FORM CYCLOHEXYLBENZENE HYDROPEROXIDE

[75] Inventors: Sheng-Hong A. Dai, Wallingford; Chung-Yuan Lin, Northford; Fred A. Stuber, North Haven, all of Conn.

[73] Assignee: The Upjohn Company, Kalamazoo, Mich.

[21] Appl. No.: 861,757

[22] Filed: Dec. 19, 1977

Related U.S. Application Data

[63] Continuation-in-part of Ser. No. 689,489, May 24, 1976, abandoned.

[51] Int. Cl.$^3$ .......................................... C07C 179/03
[52] U.S. Cl. .................................................. 568/573
[58] Field of Search ........................ 260/610 A, 610 B; 568/573

[56] References Cited

U.S. PATENT DOCUMENTS

| | | | |
|---|---|---|---|
| 2,430,865 | 11/1947 | Farkas et al. | 260/610 B |
| 2,776,320 | 1/1957 | Thompson et al | 260/610 B |
| 2,796,439 | 6/1957 | Berneis | 260/610 B |
| 2,798,096 | 7/1957 | Baumgarten | 260/610 B |
| 3,959,381 | 5/1976 | Arkell et al. | 260/610 B |

*Primary Examiner*—Werren B. Lone
*Attorney, Agent, or Firm*—Denis A. Firth; John Kekich

[57] ABSTRACT

Cyclohexylbenzene and dicyclohexylbenzenes are converted to the corresponding hydroperoxides in the presence of t-butyl, cumene, or p-diisopropylbenzene hydroperoxides and a free radical initiator. The use of the combination of hydroperoxide and free radical initiator enables the reaction to be carried out at lower temperatures (80°–105° C.) than can be employed with hydroperoxides or free radical initiators alone and gives high (90%) selectivity and good conversion (20% or higher).

4 Claims, No Drawings

PROCESS FOR THE AUTOXIDATION OF CYCLOHEXYLBENZENE TO FORM CYCLOHEXYLBENZENE HYDROPEROXIDE

This application is a continuation-in-part of our co-pending application Ser. No. 689,489 filed May 24, 1976, now abandoned.

BACKGROUND OF THE INVENTION

1. Field of the Invention

This invention relates to an improved process for the preparation of cycloalkyl aromatic hydroperoxides and is more particularly concerned with an improved process for the preparation of cyclohexylbenzene hydroperoxide and dicyclohexylbenzene dihydroperoxides.

2. Description of the Prior Art

It is known that cyclohexylbenzene can be converted to cyclohexylbenzene hydroperoxide by the autoxidation of cyclohexylbenzene in the absence of any catalyst; see U.S. Pat. No. 3,846,499. The latter process requires a first reaction temperature of 130° to 150° C. for 1 to 3 hours followed by a second reaction temperature of 105° C. to 125° C. for 2 to 4 hours. The selectivity is relatively low (of the order of 80 percent) because cyclohexylbenzene hydroperoxide can either decompose to 1-phenylcyclohexanol or rearrange to benzoylpentane derivatives.

It is also known that the autoxidation of cyclohexylbenzene can be carried out in the presence of a number of catalysts including t-butyl hydroperoxide; see Furukawa, Nenryo Kyokai-shi 40 (9), 711, 1961. The reaction was carried out at 110° C. and the conversion was low (10.3%) with no details given of selectivity to the desired hydroperoxide.

Because of the nature of the autoxidation reaction, with formation of hydroperoxides which are potentially dangerous to handle in large scale operations, it is desirable to keep the reaction temperature as low as possible but at the same time to obtain satisfactory yields of cyclohexylbenzene hydroperoxide coupled with high selectivity of the latter in the overall reaction product.

We have now found that these objectives can be achieved by use of a free radical initiator in cooperation with certain hydroperoxides in the autoxidation of cyclohexylbenzene and dicyclohexylbenzenes as will be described in more detail hereinafter.

SUMMARY OF THE INVENTION

This invention comprises a process for the autoxidation of mono- and dicyclohexylbenzenes in the presence of a hydroperoxide selected from the class consisting of t-butyl, cumene and p-diisopropylbenzene hydroperoxides to yield the corresponding hydroperoxides wherein the improvement comprises carrying out the reaction in the presence of a catalytic amount of a free radical initiator and at a temperature in the range of about 80° C. to about 105° C.

The cyclohexylbenzene hydroperoxide which is produced in accordance with the invention is useful as an intermediate in the formation of phenol and cyclohexanone. The latter rearrangement can be achieved by processes well-known in the art; see, for example, S. Furukawa, supra, M. I. Farberov et al., Zh. Org. Khim., 10 (1) 50 (1974), and M. I. Farberov et al., U.S.S.R., 422, 181 (1974): C.A. 81 169291d (1974). The dicyclohexylbenzene dihydroperoxides which are also produced in accordance with the invention are useful as intermediates in the formation of cyclohexanone and the corresponding dihydroxybenzene. Thus, p-dicyclohexylbenzene dihydroperoxide, when submitted to rearrangement using conventional procedures such as that set forth above, yields a mixture of cyclohexanone and hydroquinone. m-Dicyclohexylbenzene dihydroperoxide under the same conditions of rearrangement yields a mixture of cyclohexanone and resorcinol.

The process of the invention therefore constitutes a significant improvement in a key step in the overall conversion of benzene to phenol and related hydroxybenzenes. The overall process comprises the hydrodimerization of benzene by known procedures to form cyclohexylbenzene as the major product and dicyclohexylbenzenes as a minor product of the same reaction. The cyclohexylbenzene and dicyclohexylbenzenes, after separation if desired, are then submitted to the process of the present invention and the hydroperoxides are rearranged as set forth above to produce phenol and or hydroquinone and or resorcinol.

DETAILED DESCRIPTION OF THE INVENTION

The process of the invention is carried out conveniently by admixing the cyclohexylbenzene or dicyclohexylbenzene with the appropriate hydroperoxide. (i.e. one of the three named above) and maintaining the mixture at a temperature in the range of about 80° C. to about 105° C., in the presence of oxygen or a gaseous mixture rich in oxygen such as air. The free radical initiator is added to the mixture so obtained and the reaction temperature is maintained in the above range until the end point of the reaction is reached. The end point is the point at which the initially fast rate of formation of hydroperoxide begins to subside. The end point is readily determined by routine analytical procedures, such as high pressure liquid chromatography (HPLC), infrared or nuclear magnetic resonance spectroscopy, carried out on an aliquot.

The resulting product is then worked up using conventional isolation procedures. Illustratively, in the case where t-butyl or cumene hydroperoxide has been used as catalyst, the mixture is subjected to distillation, advantageously under reduced pressure, to recover the hydroperoxide catalyst and the unreacted cyclohexylbenzene. In the case where diisopropylbenzene hydroperoxide has been used as catalyst the latter normally crystallizes upon cooling the reaction mixture and can be removed by filtration before distilling the filtrate to recover unreacted cyclohexylbenzene. The residual cyclohexylbenzene hydroperoxide or dicyclohexylbenzene dihydroperoxide can, if desired, be purified by conventional procedures such as column chromatography or fractional recrystallization. In general, such purification is unnecessary and the crude product can be submitted, without purification, to rearrangement to produce the desired hydroxybenzene and cyclohexanone in the manner discussed above.

The amount of tertiary-butyl, cumene, or diisopropylbenzene hydroperoxide employed in the above reaction is generally not more than about 6 weight percent of cyclohexylbenzene or dicyclohexylbenzene, although higher proportions can be used if desired. Preferably, the amount of tertiary-butyl, cumene, or diisopropylbenzene hydroperoxide employed in the reaction is within the range of about 2 percent to about 5 percent by weight based on cyclohexylbenzene or dicyclohexylbenzene. The actual amount employed varies with the reaction temperature; the higher the temperature, the lower the amount of catalyst used within the limits set forth above. The amount of tertiary-butyl, cumene, or diisopropylbenzene hydroperoxide actually consumed in the reaction is very small and is within the range of about 0.4 percent to about 0.1 percent by weight based on cyclohexylbenzene or dicyclohexylbenzene employed as starting material. Some 90 percent by weight or even higher amounts of catalyst are generally recovered.

The amount of free radical initiator employed in the process of the invention is catalytic and advantageously is within the range of about 0.1 percent to about 5 percent by weight based on cyclohexylbenzene or dicyclohexylbenzene employed as starting material. Preferably, the amount of free radical initiator employed in the reaction is within the range of about 0.5 percent to about 1.0 percent by weight based on cyclohexylbenzene or dicyclohexylbenzene.

The free radical initiator employed in the process of the invention can be any of the azo type free radical initiators described in Encyclopedia of Polymer Science and Technology, Volume 2, page 278 et seq., 1965 or any of the peroxide or hydroperoxide type free radical initiators described in the same publication at Volume 9, page 814 et seq., 1968. Illustrative of azo type free radical initiators are 2,2′-azobis(aliphatic nitriles) such as 2,2′-azobisisopropionitrile, 2,2′-azobisisobutyronitrile, 2,2′-azobishexanonitrile, and the like, and bisazoalkanes such as 1,1′-azobisbutane, 1,1′-azobishexane, 1,1′-azobisoctane, and the like. Illustrative of peroxide type free radical initiators are alkyl-aromatic peroxides such as dicumyl peroxide, and the like; dialkyl peroxides such as di-t-butyl peroxide, diisobutyl peroxide, diisopropyl peroxide, diisohexyl peroxide, and the like; diperoxy ketals such as 2,2-bis(t-butylperoxy)butane, n-butyl 4,4-bis(t-butylperoxy) valerate, and the like; diacyl peroxides such as dibenzoyl peroxide, diacetyl peroxide, dilauroyl peroxide, dipropionyl peroxide, and the like; peroxy esters such as t-butyl peroxypivalate, t-butyl peroxyacetate, t-butyl peroxybenzoate, and the like; dialkyl peroxydicarbonates such as di-isobutyl peroxydicarbonate, dihexyl peroxydicarbonate, and the like; ketone peroxides such as methyl ethyl ketone peroxide, cyclohexanone peroxide, and the like.

A preferred group of free radical initiators for use in the process of the invention is azobisisobutyronitrile, t-butyl perbenzoate, and dicumyl peroxide.

As set forth above, the use of free radical initiators in accordance with the process of the invention enables the autoxidation of cyclohexylbenzene and or dicyclohexylbenzenes to be carried out at significantly lower temperatures than hitherto employed and to obtain good conversion of the starting materials to the corresponding hydroperoxides with a high degree of selectivity. As will be seen from the data set forth in the Examples below, the use of reaction temperatures higher than about 105° C. results in deterioration in the degree of selectivity, particularly when t-butyl hydroperoxide is employed as a catalyst. It will also be seen that use of the t-butyl, cumene or diisopropylbenzene hydroperoxides without the free radical initiator, or the use of the latter without the hydroperoxides, gives markedly inferior results than does the use of the combination of hydroperoxide and initiator. The use of this combination permits much faster reaction times in addition to improved yields and high selectivity. Further, the reaction temperatures which are employed in the process of the invention, unlike the higher reaction temperatures employed hitherto, do not result in decomposition of the hydroperoxides employed in the catalyst combination. The ability to recover the hydroperoxide catalysts for reuse in subsequent oxidations makes possible a significant reduction in raw material costs of the overall process.

The process of the invention can also be accomplished by forming the cumene hydroperoxide or the diisopropylbenzene dihydroperoxide in situ in the reaction mixture rather than employing the preferred hydroperoxides. This can be achieved by carrying out the process of the invention as described hereinabove but adding cumene or diisopropylbenzene to the initial reaction mixture in place of the corresponding hydroperoxides. The amounts of cumene or diisopropylbenzene employed in this embodiment of the process of the invention are within the same range, on a percentage weight basis, as that quoted above for the corresponding hydroperoxides.

The following examples describe the manner and process of making and using the invention and set forth the best mode contemplated by the inventors of carrying out the invention but are not to be construed as limiting.

EXAMPLE 1

A series of experiments were carried out using varying amounts of the various free radical initiators listed in Table I in the autoxidation of cyclohexylbenzene in the presence of catalytic amounts of tertiary-butyl hydroperoxide (the amount used in each run is shown in Table I). The following standard procedure was used in all runs:

The cyclohexylbenzene (16.01 g.:0.1 mole) was charged to a three-necked round bottomed flask fitted with stirrer, thermometer, gas inlet and reflux condenser. The flask and contents were heated to the desired temperature (see Table I) and a stream of dry oxygen at a flow rate of circa 5 ml/min. was introduced. Thereafter, the required amounts (see Table I) of tertiary-butyl hydroperoxide and the free radical initiator were introduced with vigorous stirring. The temperature of the reaction mixture was maintained at the above temperature with stirring and the progress of the reaction was monitored by HPLC analysis of aliquots of the mixture. When the rate of formation of the desired cyclohexylbenzene 1-hydroperoxide slowed significantly, the reaction mixture was cooled to room temperature. The tertiary-butyl hydroperoxide and unreacted cyclohexylbenzene were removed by distillation under reduced pressure. An aliquot of the residue was analyzed by high pressure liquid chromatography to determine the proportion of desired cyclohexylbenzene hydroperoxide and principal by-products. The residue was then diluted with hexane (5 ml.) and allowed to stand at 0° C. whereupon the cyclohexybenzene 1-hydroperoxide separated as a crystalline solid having a melting point of 61° C.

The data given in Table I below shows the identity and amount of each free radical initiator, the amount of tertiary-butyl hydroperoxide (TBHP), the reaction temperature and time of reaction, the % conversion (determined by amount of cyclohexylbenzene recovered) and the distribution of products in the crude residue from the reaction (determined by quantitative analysis using HPLC). The cyclohexylbenzene 1-hydroperoxide is shown as "P" and the two principal impurities as "P-1" and "P-2". The by-product "P-1" is a mixture of cyclohexylbenzene 2-hydroperoxide and 1-phenylcyclohexanol and the by-product "P-2" is a mixture of 5-benzoylpentyl hydroperoxide and 5-benzoylpentanol. The first run shown in Table I was a control experiment carried out in the absence of free radical initiator to illustrate the lower level of conversion achieved under identical conditions.

The results of Runs 4 and 6, which were carried out at temperatures above 105° C., as compared with Run 5, carried out at reaction temperature within the presently claimed range of this invention, dramatically illustrate the drop in degree of selectivity which results from the use of the higher temperatures.

A second series of experiments was carried out, using exactly the procedure described above but using double the amount of phenylcyclohexane employed (i.e. 32 g. in place of 16.01 g.), to show the effect of using free radical initiators alone, i.e. in the absence of t-butyl, cumene or diisopropylbenzene hydroperoxides. The results are shown in Table II and it is clearly apparent that the use of the free radical initiators alone gives much lower conversion and a markedly lower degree of selectivity (the yields in Runs 9 and 10 were so low that no analysis of the oxidation product, to determine selectivity, was possible).

(see Example 1) were found to be 4.8 and 3.6 percent, respectively.

EXAMPLE 3

A mixture of 32.1 g. (0.2 mole) of cyclohexylbenzene, and 1.3 g. (4 percent by weight) of tertiary-butyl hydroperoxide was heated to 100°±3° C. and maintained thereat while oxygen was bubbled into the mixture at a rate of circa 5 ml. per minute and 0.65 g. (2 percent by weight) of tertiary-butyl perbenzoate and 0.65 g. (2 percent by weight) of sodium adipate (present to neutralize the acid generated by the perbenzoate) were added. The mixture was maintained for 7 hours at the above temperature. At the end of this time it was found by high pressure liquid chromatography that 17.5 percent of the cyclohexylbenzene had been oxidized with a selectivity to cyclohexylbenzene hydroperoxide of 91.7 percent.

EXAMPLE 4

The procedure described in Example 3 was repeated with the sole exception that the tertiary-butyl perbenzoate employed as initiator was replaced by 0.64 g. (2 percent by weight) of dicumyl peroxide and the sodium adipate was omitted. After 7.5 hours of reaction at 105°±2° C. it was found that 19.1 percent of the cyclohexylbenzene had been oxidized with a selectivity to

TABLE I

| Run | Initiator (wt. %) | TBHP (wt. %) | Reaction temp. (°C.) | Reaction Time (hr.) | % Conversion | Product Distribution % w/w | | |
|---|---|---|---|---|---|---|---|---|
| | | | | | | P | P-1 | P-2 |
| 1 | 0 (0) | 5 | 100 ± 3 | 8 | 11.4 | 90.5 | 4.7 | 4.8 |
| 2 | dibenzoyl peroxide (1.0) | 5 | 98 ± 2 | 7.5 | 15.1 | 86.1 | 9.1 | 4.8 |
| 3 | dibenzoyl peroxide (2.0) | 5 | 98 ± 2 | 5 | 17.8 | 91.5 | 5.8 | 2.7 |
| 4 | 2,2'-azobisisobutyronitrile (2) | 4.0 | 115 ± 2 | 5.5 | 24.5 | 87.7 | 7.3 | 5.1 |
| 5 | 2,2'-azobisisobutyronitrile (2) | 5.0 | 100 ± 2 | 7.0 | 20.0 | 91.5 | 5.8 | 4.7 |
| 6 | 2,2'-azobisisobutyronitrile (2) | 2.0 | 115 ± 2 | 7.0 | 23.1 | 87.0 | 8.0 | 5.0 |
| 7 | t-butyl perbenzoate (2) | 4.0 | 100 ± 3 | 6.0 | 17.5 | 91.7 | 6.4 | 1.9 |
| 8 | cumene peroxide (2) | 4.0 | 100 ± 2 | 8.0 | 15.0 | 92.0 | 4.3 | 3.7 |

TABLE II

| Run No. | Initiator (wt. %) | Reaction temp. (°C.) | Reaction time (hr.) | % Conversion | Product Distribution % w/w | | |
|---|---|---|---|---|---|---|---|
| | | | | | P | P-1 | P-2 |
| 9 | 2,2'-azobisisobutyronitrile (2) | 100 ± 3° C. | 7.0 | 4.4 | — | — | — |
| 10 | dicumyl peroxide (2) | 100 ± 3° C. | 6.0 | 1.6 | — | — | — |
| 11 | t-butyl perbenzoate (2) | 100 ± 3° C. | 7.5 | 9.2 | 85.7 | 4.8 | 9.6 |
| 12 | benzoyl peroxide (2) | 100 ± 3° C. | 7.5 | 10.8 | 83.0 | 6.2 | 10.8 |

EXAMPLE 2

A mixture of 32.1 g. (0.2 mole) of cyclohexylbenzene and 1.6 g. (5 percent by weight) of tertiary-butyl hydroperoxide was heated to 80° C. and maintained thereat while oxygen was bubbled into the mixture at a rate of circa 5 ml. per minute and 0.16 g. (0.5 percent by weight) of azobis-isobutyronitrile was added. The progress of the reaction was monitored hourly using high pressure liquid chromatography. Two further additions of azobis-isobutyronitrile, each of 0.16 g., were made at the end of 60 minutes and 180 minutes from the time of the first addition. After 7 hours of reaction, with the temperature maintained at 80° C. throughout, it was found by high pressure liquid chromatography that 16 percent of the cyclohexylbenzene had been oxidized with a selectivity to cyclohexylbenzene hydroperoxide of 91.8 percent. The amounts of impurities P-1 and P-2 cyclohexylbenzene hydroperoxide of 92.3 percent.

EXAMPLE 5

For purposes of comparison the following run was carried out in the absence of initiator and using a higher reaction temperature than that employed in any of the examples set forth above.

A mixture of 65 g. (0.4 mole) of cyclohexylbenzene and 1.3 g. (2 percent by weight) of tertiary-butyl hydroperoxide was kept at 120° C. and oxygen was bubbled through the reaction mixture at circa 5 ml./minute. At the end of 5 hours heating at the above temperature it was found by high pressure liquid chromatography that 24.7 percent conversion of the cyclohexylbenzene had taken place but the selectivity to cyclohexylbenzene hydroperoxide was only 86.9 percent. The amounts of impurities P-1 and P-2 (see Example 1) were 7.1 and 6 percent, respectively.

EXAMPLE 6

A mixture of 51.2 g. (0.21 mole) of p-dicyclohexylbenzene, 2 g. (3.9 percent by weight) of tertiary-butyl hydroperoxide, 0.56 g. (1 percent by weight) of tertiary-butyl perbenzoate, and 15 ml. of benzene was heated at 105° to 108° C. in the presence of a stream of oxygen (circa 5 ml. per minute). The progress of the reaction was monitored by high pressure liquid chromatography. The reaction was discontinued after 11 hours and the benzene was removed by distillation under reduced pressure. To the residual product was added 100 ml. of methanol and the mixture was allowed to stand at 0° C. The unreacted p-dicyclohexylbenzene (35.9 g: 70.2 percent recovery) which crystallized was isolated by filtration. The methanolic mother liquors were evaporated to remove methanol and the residue was dissolved in 100 ml. of ether and extracted with an excess of 50 percent aqueous sodium hydroxide. The aqueous extract was neutralized by bubbling carbon dioxide therethrough and extracted with three portions, each of 20 ml., of ether. The ether extracts were combined and dried over anhydrous magnesium sulfate and then evaporated to dryness to give 1.75 g. of dicyclohexylbenzene dihydroperoxide.

The ethereal solution remaining from the original reaction mixture after extraction with the sodium hydroxide solution was washed with water and dried over anhydrous magnesium sulfate. The dried extract was evaporated to dryness to obtain 8.81 g. of dicyclohexylbenzene monohydroperoxide.

The dicyclohexylbenzene hydroperoxide obtained as described above was rearranged to yield hydroquinone and cyclohexanone using the following procedure.

To a suspension of 1.7 g. of dihydroperoxide in 15 ml. of anhydrous benzene was added with stirring 6 drops of boron trifluoride etherate while the temperature was kept below 40° C. The mixture turned light green and the undissolved portion of the dihydroperoxide rapidly disappeared. The mixture was stirred at room temperature (circa 20° C.) for 1 hour before being cooled to 0° C. and filtered. The hydroquinone so isolated was dried; 0.51 g. (63.75 percent theoretical yield). The mother liquors were shown by high pressure liquid chromatography to contain cyclohexanone and some additional hydroquinone.

EXAMPLE 7

A mixture of 32.2 g. (0.2 mole) of cyclohexylbenzene, 1.6 g. (5 percent by weight) of cumene hydroperoxide and 0.65 g. (2 percent by weight) of tertiary-butyl peroxybenzoate was heated at 100°±2° C. and oxygen was bubbled through the mixture at circa 5 ml. per minute. After a total of 21.5 hours heating at the above temperature, it was found by high pressure liquid chromatography that 25 percent of the cyclohexylbenzene had been oxidized with a selectivity of 88 percent to cyclohexylbenzene hydroperoxide.

We claim:

1. A process for the autoxidation of cyclohexylbenzene to form cyclohexylbenzene hydroperoxide which comprises heating cyclohexylbenzene at a temperature in the range of about 80° C. to about 105° C. in the presence of oxygen and from about 2 to 6 percent by weight, based on cyclohexylbenzene, of a hydroperoxide selected from the class consisting of tertiary-butyl and cumene hydroperoxides and p-diisopropylbenzene dihydroperoxide, and from about 0.1 to 5 percent by weight, based on cyclohexylbenzene, of a free radical initiator selected from the group consisting of azobisisobutyronitrile, t-butylperbenzoate and dicumyl peroxide.

2. The process of claim 1 wherein the free radical initiator is azobisisobutyronitrile and the hydroperoxide is tertiary-butyl hydroperoxide.

3. The process of claim 1 wherein the free radical initiator is t-butyl perbenzoate.

4. The process of claim 1 wherein the free radical initiator is di-cumyl peroxide.